United States Patent [19]

Young

[11] Patent Number: 5,470,868
[45] Date of Patent: Nov. 28, 1995

[54] METHODS FOR TREATING EMESIS AND NAUSEA USING OPTICALLY PURE R(+) ONDANSETRON

[75] Inventor: James W. Young, Palo Alto, Calif.

[73] Assignee: Sepracor Inc., Marlborough, Mass.

[21] Appl. No.: 164,734

[22] Filed: Dec. 7, 1993

Related U.S. Application Data

[63] Continuation of Ser. No. 750,387, Aug. 27, 1991, abandoned, which is a continuation-in-part of Ser. No. 721,868, Jun. 26, 1991, abandoned.

[51] Int. Cl.$^6$ ................................. A61K 31/415
[52] U.S. Cl. ........................... 514/397; 514/872
[58] Field of Search .................... 424/451; 514/397, 514/872

[56] References Cited

U.S. PATENT DOCUMENTS

| | | | |
|---|---|---|---|
| 4,695,578 | 9/1987 | Coates et al. | 514/397 |
| 4,721,720 | 1/1988 | Wootton et al. | 514/304 |
| 4,749,718 | 6/1988 | Coates et al. | 514/397 |
| 4,753,789 | 6/1988 | Tyers et al. | 424/10 |
| 4,783,478 | 11/1988 | Wootton et al. | 514/397 |
| 4,835,173 | 5/1989 | Tyers | 514/397 |
| 4,845,115 | 7/1989 | Tyers | 514/397 |
| 4,847,281 | 7/1989 | Tyers | 514/397 |
| 4,851,407 | 7/1989 | Wootton et al. | 514/213 |
| 4,929,632 | 5/1990 | Tyers et al. | 514/397 |
| 4,983,621 | 1/1991 | Bunce et al. | 514/397 |

FOREIGN PATENT DOCUMENTS

| | | | |
|---|---|---|---|
| 0201165A3 | 11/1986 | European Pat. Off. | |
| 8501889 | 8/1985 | United Kingdom | C07D 403/06 |
| 8717353 | 1/1988 | United Kingdom | C07D 403/06 |
| WO93/00075 | 1/1993 | WIPO | |

OTHER PUBLICATIONS

Ariëns, E. J., "Racemic therapeutics—ethical and regulatory aspects", *Eur J Clin Pharmacol* 41: 89–93 (1991).
Ariëns, E. J., "Racemische therapeutica probleemmiddelen", *Pharmaceutisch Weekblad* 125(22): 552–554 (1990) (with English abstract).
Ariëns, E. J., "Stereoselectivity in pharmacodynamics and pharmacokinetics", *Schweiz. Med. Wschr.* 120(5): 131–134 (1990).
Butler et al., "The pharmacological characterization of 5–HT$_3$ receptors in three isolated preparations derived from guinea–pig tissues", *Br. J. Pharmacol.* 101:591–598 (1990).
Hibert et al., "Conformation–Activity Relationship Study of 5–HT$_3$ Receptor Antagonists and a Definition of a Model for This Receptor Site", *J. Med. Chem.* 33: 1594–1600 (1990).
Testa et al., "Racemates Versus Enantiomers in Drug Development: Dogmatism or Pragmatism?", *Chirality* 2: 129–133 (1990).
Jamali et al., *J. Pharm Sci.* 78(9): 695–715 (1989).

(List continued on next page.)

*Primary Examiner*—Marianne M. Cintins
*Assistant Examiner*—K. E. Weddington
*Attorney, Agent, or Firm*—Pennie & Edmonds

[57] ABSTRACT

Methods are disclosed utilizing the optically pure R(+) isomer of ondansetron. This compound is a potent drug for the treatment of nausea and vomiting associated with chemotherapy and radiation therapy, while avoiding the concomitant liability of adverse effects associated with the racemic mixture of ondansetron. The R(+) isomer of ondansetron is also useful for the treatment of behavioral disorders such as mood anxiety and schizophrenia, and such other conditions as may be related to R(+) ondansetron's activity as a competitive antagonist of serotonin receptor subtype 5-HT$_3$ such as disorders of gastrointestinal motility, depression, migraine, and as an aid for alcohol withdrawal, nicotine withdrawal, and drug (benzodiazepine et al.) withdrawal, without the concomitant liability of adverse effects associated with the racemic mixture of ondansetron. Furthermore, the R(+) isomer of ondansetron is also useful for the treatment of cognitive disorders such as dementia or age-associated memory impairment, while avoiding the concomitant liability of adverse effects associated with the racemic mixture of ondansetron.

9 Claims, No Drawings

OTHER PUBLICATIONS

Butler et al., *Br. J. Pharamcol.*, 94: 397–412 (1988).
Kris et al., *J. Clin. Oncol.*, 6(4): 659–662 (1988).
Tyers et al., *Eur. J. Cancer*, 25:(Suppl. 1) S15–S19 (1989).
Grunberg et al., *J. Clin. Oncol.*, 7(8): 1137–1141 (1989).
Schmoll, H. J., *Eur. J. Clin. Oncol.*, 25:(Suppl. 1) S35–S39 (1989).
Khojasteh et al., *Cancer*, 66(6): 1101–1105 (1990).
Marty M., *Eur. J. Cancer Clin. Oncol.*, 25:(Suppl. 1) S41–S45 (1989).
De Mulder et al., *Annals Intern. Med.*, 113:(11) 834–840 (1990).
Green et al., *Cancer Chemother. Pharmacol.*, 24: 137–139 (1989).
Cubeddu et al., *New Engl. J. Med.*, 322(12): 810–816 (1990).
Smyth J. F., *Eur. J. Cancer Clin. Concol.*, 25: (Suppl. 1) S55–S57 (1989).
Graves, T., *DICP, Ann. Pharmacother*, 24(11): (Suppl.) S51–S54 (1990).
Williston Park, *Oncology*, 4(9): 98, 102 (1990).
Priestman et al., *Clin. Oncol.*, 2: 71–75 (1990).
Costall et al., *Pharmacol. Biochem. Behavior*, 36(1): 97–104 (1990).
Merrifield et al., *Clin. Pharm.*, 8(3): 187–199 (1989).
Van Liessum et al., *Eur. J. Cancer*, 26(6): 767–770 (1990).
*Hosp. Formul.*, 25(3): 260 (1990).
Grunberg S. M., *New Engl. J. Med.*, 322(12): 846–848 (1990).
Cunningham et al., *Lancet*, Jun. 27, 1987, 1461–1463.
*Lancet*, Jun. 27, 1987, 1470–1471.
Scrip No. 1626, Jun. 29, 1991, 24–26.

METHODS FOR TREATING EMESIS AND NAUSEA USING OPTICALLY PURE R(+) ONDANSETRON

This application is a continuation of application Ser. No. 07/750,387, filed Aug. 27, 1991, now abandoned, which is a continuation-in-part of application Ser. No. 07/721,868, filed Jun. 26, 1991, now abandoned.

BACKGROUND OF THE INVENTION

This invention relates to novel compositions of matter containing optically pure R(+) ondansetron. These novel compositions have potent antiemetic activity and are useful in ameliorating the nausea and vomiting otherwise induced by cancer chemotherapeutic agents and higher dose radiotherapeutic treatment procedures while avoiding adverse effects including but not limited to headache, constipation and increases in transaminase levels, which are associated with the administration of the racemic mixture of ondansetron. Additionally, these novel compositions of matter containing optically pure R(+) ondansetron are useful in treating behavioral disorders such as mood anxiety and schizophrenia, and such other conditions as may relate to R(+) ondansetron's activity as a competitive antagonist of serotonin receptor subtype 5-HT$_3$, including but not limited to disorders of gastrointestinal motility, depression, migraine, alcohol, nicotine or drug (benzodiazepine et al.) withdrawal, while avoiding adverse effects associated with the administration of the racemic mixture of ondansetron. Furthermore, these novel compositions of matter containing optically pure R(+) ondansetron are useful in treating cognitive disorders such as dementia and age-associated memory impairment, while avoiding the adverse effects associated with the administration of the racemic mixture of ondansetron. Also disclosed are methods for treating the above described conditions in a human while avoiding the adverse effects that are associated with the racemic mixture of ondansetron, by administering the R(+) isomer of ondansetron to said human.

The active compound of this composition, and method is an optical isomer of the compound, ondansetron which is described in U.S. Pat. No. 4,695,578. Chemically, the active compound is the R(+) isomer of 1,2,3,9-tetrahydro-9-methyl-3-[(2-methyl-1-H-imidazol-1-yl)methyl]-4H-carbazol-4-one. This isomer will hereinafter be referred to as R(+) ondansetron.

Steric Relationships and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, and that the corresponding L-enantiomer, a potent teratogen.

Ondansetron, which is the subject of the present invention, is available commercially only as the 1:1 racemic mixture; i.e., it is a mixture of optical isomers, called enantiomers. The racemic mixture of ondansetron is a dihydrate, that is administered as a hydrochloride salt. The enantiomers of ondansetron are disclosed in Butler et al., Br. J. Pharmacol., 94, pg. 397–412 (1988). This reference states that the R and S isomers of ondansetron were approximately equipotent as 5-HT antagonists on rat vagus nerve. Furthermore, the reference alleges that the racemic mixture caused concentration-dependent parallel rightward displacement of the 2-methyl -5-HT concentration response curve when exposed to the longitudinal smooth muscle of the guinea-pig ileum, and that the R isomer was more potent than the S isomer when administered competitively against 2-methyl-5-HT.

The racemic mixture of ondansetron is an antagonist of the 5-hydroxytryptamine (5-HT$_3$ or serotonin) receptor. The role of serotonin, and thus the pharmacology of ondansetron has been broadly implicated in a variety of conditions for many years (see, Phillis, J. W., The Pharmacology of Synapses, Pergamon Press, Monograph 43, 1970; Frazer, A. et al. Annual Rev. of Pharmacology and Therapeutics 30, 307–348, 1990). Thus, research has focused on locating the production and storage sites of serotonin as well as the location of serotonin receptors in the human body in order to determine the connection between these sites and various disease states or conditions.

In this regard, it was discovered that a major site of production and storage of serotonin is the enterochromaffin cell of the gastrointestinal mucosa. It was also discovered that serotonin has a powerful stimulating action on intestinal motility by stimulating intestinal smooth muscle, speeding intestinal transit, and decreasing absorption time., as in diarrhea. This stimulating action is also associated with nausea and vomiting.

Thus, researchers studied diseases and treatment of diseases where the above described effects were manifested. One such treatment is chemo-and radio-therapy of cancer using chemotherapeutic and high dose radiotherapeutic agents. Chemo-and radio-therapy may induce nausea and vomiting by the release of serotonin from damaged enterochromaffin cells in the gastrointestinal tract. Release of the neurotransmitter serotonin, stimulates both afferent vagal nerve fibers (thus initiating the vomiting reflex) and serotonin receptors in the chemoreceptor trigger zone of the area postrema region of the brain.

One of the first agents used to prevent the nausea and vomiting associated with emetogenic cancer chemotherapy was metoclopramide. This compound is an antagonist of central and peripheral dopamine receptors, and at high doses it also antagonizes serotonin receptors. Because it had this combined effect, researchers began to search for a more specific and safer serotonin 5-HT$_3$ antagonist to use to treat nausea and vomiting associated with chemo-and radio-therapy of cancer. This led to the development of ondansetron.

Ondansetron is a competitive antagonist at serotonin 5-HT$_3$ receptor subtypes in both the gastrointestinal tract and the brain, where it blocks both sites of serotonin-induced emesis. With respect to its anti-emetic potential, ondansetron appears to offer a dual mode of action through antagonism of serotonin at peripheral vagal nerve afferents, and antagonism of serotonin within the central nervous system, at or near the chemoreceptor trigger zone.

Consequently, ondansetron may produce a significant reduction, or a complete inhibition of nausea and vomiting in the majority of patients subsequently treated with cancer chemotherapeutics of moderate or high emetic potential. Similarly, the compound prevented radiation-induced nausea and emesis. Further, ondansetron appears to have an effect on gastrointestinal motility slowing the transit of material through portions of the tract. This decrease in motility may be beneficial in those patients undergoing the chemotherapy for cancer where diarrhea can provide an additional debilitating burden.

Ondansetron's use as an antiemetic by either the intravenous or oral routes is disclosed in U.S. Pat. Nos. 4,753,789 and 4,929,632. Furthermore, various researchers have tested the use of the racemic mixture of ondansetron to prevent nausea and vomiting caused by anticancer chemotherapy. See, Green et al., *Cancer Chemother. Pharmacol.*, 24:137–139 (1989); Cubeddu et al., *New Engl. J. Med.*, Vol. 322; No. 12, pg. 810–815 (1990); De Mulder et al., *Ann. Int. Med.*, Vol. 113: No. 11, pg. 834–840 (1990); Marty, *Eur. J. Cancer Clin. Oncol.*, Vol. 25, Suppl. 1, pg. 541–545 (1989); Khojasteh et al., *Cancer*, Vol. 66, No. 6, pg. 1101–1105 (1990); Schmoll, *Eur. J. Cancer Clin. Oncol.*, Vol. 25, Suppl. 1, pg. 535–539 (1989); Grunberger et al., *J. Clin. Oncol.*, vol. 7, No. 8, pg. 1137–1141 (1989); Kris et al., *J. Clin. Oncol.*, Vol. 6, no. 4, pg. 659–662 (1988).

Thus, in the context of adjunctive therapy for cancer treatment, ondansetron appears to be an effective antiemetic, although its dose-response relationships remain to be clarified. The drug offers a moderate potency, a half-life of some three hours, and the potential for prophylactic/therapeutic activity. Dosing 1–2 hours prior to cancer therapy or at the initiation of therapy can be accomplished by continuous infusion, or repeated oral or intravenous administrations. (see Smith, R. N., Safety of Ondansetron, European J. of Cancer and Clinical Oncology, 25 Suppl.1 547–50, 1989; and Smyth, J.F. ibid., 555–57, 1989).

As stated previously, stimulation of serotonin receptors has been postulated to be involved in a variety of disease states and conditions. Thus, it has been proposed that antagonizing serotonin receptors will assist in treating these conditions.

It has been proposed that the racemic mixture of ondansetron is useful in the treatment of anxiety disorders. Anxiety disorder has its etiology in both psychologic and physiologic factors, and it has been suggested that a genetic influence exists. Emotional stress can precipitate anxiety neurosis which represents the individual's fear of losing control of such emotional drives as aggression or dependency needs, and losing control of one's resulting actions. Physiologically, anxiety is associated with autonomic nervous system discharge, and related neurohumoral processes. In acute anxiety attacks, lasting from a few minutes to an hour, the individual experiences a subjective sense of terror, for no evident reason, and perhaps a haunting dread of catastrophe. Chronic anxiety displays less intense symptoms of longer duration, characterized by uneasiness, nervousness, nagging uncertainty about future events, headache, fatigue and subacute autonomic symptoms. The use of the racemic mixture of ondansetron to treat anxiety disorders is disclosed in U.S. Pat. No. 4,695,578.

It has also been proposed that the racemic mixture of ondansetron is useful to treat psychotic disorders such as schizophrenia. (See U.S. Pat. No. 4,695,578). Schizophrenic disorders are complex mental disorders which tend toward chronicity, and which impair functioning, and are characterized by psychotic symptoms of disturbed thinking, feeling and general behavior. Clear, goal directed thought becomes difficult, while blunting and inappropriate affect become the most characteristic emotional changes. Auditory hallucinations can be common, and delusions of persecution are frequent, as are threats of violence, and minor aggressive outbursts. Disturbances of movement can range from significant over-activity and excitement to retardation and stupor. Treatment has often included tranquilizer and other antipsychotic drugs, administered orally or by long acting depot injections (to offset problems of patient compliance).

The racemic mixture of ondansetron has also been proposed to be useful in the treatment of depression (see U.S. Pat. No. 4,835,173). Depression, an affective disorder, is characterized by changes in mood, as a primary clinical feature. The most common of the significant mental illnesses, depression must be distinguished clinically from periods of normal grief, sadness, and disappointment, and the related dysphoria or demoralization frequently associated with medical illness. Depression is characterized by feelings of intense sadness, and despair, mental slowing and loss of concentration, pessimistic worry, agitation, and self-deprecation. Physical changes can also occur, including insomnia, anorexia, and weight loss, decreased energy and libido, and the disruption of circadian rhythms. Often the condition responds well to tricyclic or related antidepressant drugs, monoamine oxidase inhibitors, or in resistant cases or severe disease, to electro-convulsive shock treatment. Nevertheless, the treatment of depression would benefit from new therapy.

It has also been proposed that the racemic mixture of ondansetron is useful to treat migraine (see U.S. Pat. No. 4,695,578). Migraine is of unknown cause, although evidence suggests a functional disturbance of the cranial circulation. The condition is a paroxysmal disorder, characterized by recurrent attacks of headache, which can be associated with visual and gastrointestinal disturbances. Migraine headaches may be preceded by a short period of depression, irritability, restlessness or anorexia.

U.S. Pat. No. 4,847,281 discloses the use of the racemic mixture of ondansetron to treat substance abuse. Disorders of substance use or abuse often involve both psychologic and physical dependence, accompanied by the development of tolerance (the need to increase the dose progressively so as to produce the effect originally achieved by smaller amounts), and manifested by a withdrawal or abstinence syndrome.

Alcohol withdrawal syndrome represents a continuum of symptoms including tremor, weakness, sweating and gastrointestinal symptoms usually beginning some hours after cessation of intake. Drugs which alter the serotonin system can modulate the alcohol consumption in humans. Some mutual, but incomplete cross-tolerance exists between alcohol and other drugs including the benzodiazepines, the sedative-hypnotic, and the anxiolytic muscle relaxant group. While benzodiazepine withdrawal symptoms are often considered moderate, in withdrawal, often anxiety returns, with dysphoria irritability, sweating, headache and sleep abnormalities. Nicotine withdrawal syndrome following cessation of tobacco use, varies significantly among subjects in intensity, and specific signs and symptoms. Apart from the craving for tobacco products, which begins within 24 hours of cessation and then subsides over a period of some days, other symptoms include, but are not limited to, irritability, anxiety, increased appetite and the gastrointestinal symptoms, and inability to concentrate.

In addition, the racemic mixture of ondansetron could be useful in the treatment of cognitive disorders. Cognitive disorders include but are not limited to dementia and age-associated memory impairment.

Dementia can occur at any age. It is a structurally caused permanent or progressive decline in several dimensions of intellectual function that interferes substantially with individual normal social or economic activity.

One particular type of dementia is Alzheimers-type dementia. Alzheimers-type dementia is thought to be due to a degenerative process, with a large loss of cells from the cerebral cortex and other brain areas. Acetylcholine-transmitting neurons and their target nerve cells are particularly affected. The brain shows marked atrophy with wide sulci and dilated Ventricles. Senile plaques and neurofibrillary tangles are present. Memory loss is the most prominent early symptom. Disturbances of arousal do not occur early in the course. Alzheimer's presenile and senile onset dementias are similar in both clinical and pathologic features, with the former commonly beginning in the 5th and 6th decades and the latter in the 7th and 8th decades. The dementia usually progresses steadily, becoming well advanced in 2 to 3 years. Some cases of dementia occurring in the presenile period are hard to classify and are sometimes labelled idiopathic or simple presenile dementia.

The signs and symptoms of dementia, in particular Alzheimers-type dementia, include depression, paranoia, anxiety or any of several other psychologic symptoms. The most common clinical picture is slow disintegration of personality and intellect due to impaired insight and judgment and loss of affect. Memory impairment increases, beginning with problems recalling recent events or finding names. The impairment varies greatly from time to time and often from moment to moment. Dementia generally is an insidious, slowly progressive, untreatable condition. However, the rate of progression varies widely and depends on the cause.

Another type of cognitive disorder is age-associated memory impairment (AAMI). AAMI is used to describe healthy non-demented people who have experienced memory loss over the course of the person's life. Most commonly it is used to describe adults over the age of 50 who have experienced memory loss over the course of adult life. It has been estimated that between 25% and 50% of people over the age of 65 have this disorder.

While the racemic mixture of ondansetron offers efficacy in treating a variety of diseased states and conditions, its use is associated with adverse effects (principally headache and constipation) which increase with the dose of the racemic mixture of ondansetron administered.

Thus it would be particularly desirable to find a compound with the advantages of ondansetron which would not have the aforementioned disadvantages.

SUMMARY OF THE INVENTION

It has now been discovered that the optically pure R(+) isomer of ondansetron is an effective anti-emetic agent, useful as an adjunctive therapy in cancer treatment to ameliorate nausea and vomiting induced by chemo- or radio-therapeutics, while decreasing the usual adverse effects including, but not limited to, headache, constipation and increases in transaminase levels which are associated with the racemic mixture of ondansetron. It has also been discovered that the optically pure R(+) isomer of ondansetron is a useful agent to treat such behavioral disorders as mood anxiety and schizophrenia, and such other conditions as may relate to the composition's activity as a competitive antagonist at serotonin receptor subtype 5-HT$_3$, such as disorders of gastrointestinal motility, depression, migraine, and as a therapeutic aid in alcohol, nicotine, and benzodiazepine withdrawal, while decreasing the usual adverse effects associated with the racemic mixture of ondansetron.

Furthermore, it has also now been discovered that the optically pure R(+) isomer of ondansetron is useful in treating cognitive disorders such as dementia and age-associated memory impairment, while decreasing the adverse effects associated with the racemic mixture of ondansetron.

The present invention also includes novel compositions of matter, containing optically pure R(+) ondansetron which are useful and effective as antiemetic adjunctive therapy in cancer treatment by chemo-or radio-therapeutics, and as agents for the aforementioned disorders. These novel compositions also avoid, or reduce the above described adverse effects associated with the administration of the racemic mixture of ondansetron. Thus, with the R(+) isomer of ondansetron, clearer dose definitions of efficacy visa vis adverse effects, may be achieved.

DETAILED DESCRIPTION OF THE INVENTION

The present invention encompasses a method of eliciting an antiemetic effect while avoiding the concomitant liability of adverse effects which comprises administering to a human in need of such antiemetic therapy an amount sufficient to alleviate nausea and vomiting, but insufficient to cause said adverse effects, of R(+) ondansetron, or a pharmaceutically acceptable salt thereof, substantially free of its S(−) stereoisomer.

The present invention also encompasses an antiemetic composition for the treatment of a human in need of antiemetic therapy, which comprises an amount sufficient to alleviate nausea and vomiting but insufficient to cause adverse effects, of R(+) ondansetron, or a pharmaceutically acceptable salt thereof, substantially free of its S(−) stereoisomer.

The present invention further encompasses a method of treating behavioral disorders such as mood anxiety or schizophrenia in a human while avoiding the concomitant liability of adverse effects, which comprises administering to said human in need of such therapy, an amount sufficient to alleviate said condition, but insufficient to cause said adverse effects, of R(+) ondansetron, or a pharmaceutically acceptable salt thereof, substantially free of its S(−) stereoisomer.

In addition, the present invention encompasses a composition for the treatment of a human with behavior disorders such as mood anxiety or schizophrenia, which comprises an amount sufficient to alleviate behavioral disorders such as mood anxiety or schizophrenia, but insufficient to cause adverse effects, of R(+) ondansetron, or a pharmaceutically acceptable salt thereof, substantially free of its S(−) stereoisomer.

Also included in the present invention is a method of treating a condition caused by disturbance of neuronal 5-HT function while avoiding the concomitant liability of adverse effects, which comprises administering to a human in need of such therapy an amount sufficient to alleviate said condition but insufficient to cause said adverse effects, of R(+) ondansetron, or a pharmaceutically acceptable salt thereof, substantially free of its S(−) stereoisomer. Conditions caused by a disturbance of neuronal 5-HT function include but are not limited to, disorders of gastrointestinal motility, depression, migraine, and alcohol, nicotine, or drug (benzodiazepine et al.) withdrawal.

A further aspect of the present invention is a composition for treating a condition caused by disturbance of neuronal 5-HT function, which comprises an amount sufficient to alleviate said condition but insufficient to cause adverse effects, of R(+) ondansetron, or a pharmaceutically acceptable salt thereof, substantially free of its S(−) stereoisomer.

Furthermore, the present invention includes a method of treating cognitive disorders such as dementia or age-associated memory impairment, while avoiding the concomitant liability of adverse effects, which comprises administering to a human in need of such therapy an amount sufficient to alleviate said cognitive disorder but insufficient to cause said adverse effects, of R(+) ondansetron, or a pharmaceutically acceptable salt thereof, substantially free of its S(−) stereoisomer.

A further aspect of the present invention is a composition for treating cognitive disorders such as dementia or age-associated memory impairment, which comprises an amount sufficient to alleviate said condition, but insufficient to cause adverse effects, of R(+) ondansetron, or a pharmaceutically acceptable salt thereof, substantially free of its S(−) stereoisomer.

The available racemic mixture of ondansetron (i.e. a 1:1 racemic mixture of stereoisomers) causes antiemetic activity, and provides therapy and a reduction of symptoms in a variety of conditions and disorders; however this racemic mixture, while offering the expectation of efficacy, causes adverse effects. Utilizing the R(+) isomer of ondansetron alone results in dose related definitions of efficacy, diminished adverse effects, and accordingly, an improved therapeutic index. It is therefore, more desirable to use the R(+) isomer of ondansetron.

The term 'adverse effects' includes, but is not limited to headache, constipation, fatigue, sedation, lethargy, drowsiness, dry mouth, diarrhea and transient increases in transaminase levels. Increases in the serum activity of certain hepatocellular enzymes is also included within the term "adverse effects".

The term "substantially free of its S(−) stereoisomer" as used herein means that the composition contains a greater proportion of the R(+) isomer of ondansetron in relation to the S(−) isomer of ondansetron. In one embodiment the term "substantially free of its S(−) stereoisomer" as used herein means that the composition contains at least 90 % by weight of R(+) ondansetron, and 10 % by weight or less of S(−) ondansetron. In the most preferred embodiment the term "substantially free of the S(−) stereoisomer" means that the composition contains at least 99 % by weight R(+) ondansetron, and 1% or less of S(−) ondansetron.

The term, "eliciting an antiemetic effect" as used herein means providing relief from the symptoms of nausea and vomiting induced spontaneously or substantially free of its associated with emetogenic cancer chemotherapy or irradiation therapy.

The term, "behavioral disorders such as mood anxiety, and schizophrenia" as used herein means relief from the symptoms which include, but are not limited to, a subjective sense of terror, a dread of catastrophe, uneasiness, nervousness uncertainty, headache, fatigue, disturbed thinking, inappropriate affect, auditory hallucinations, aggressive outbursts and the like.

The term, "a condition caused by disturbance of neuronal 5-HT function" includes but is not limited to disorders of gastrointestinal motility, depression, migraine and alcohol, nicotine or drug (benzodiazepine et al.) withdrawal. This includes relief from the symptoms which include, but are not limited to, diarrhea and related symptoms, as decreased absorption time, etc., intense sadness, despair, mental slowing, loss of concentration, worry, agitation, headache, irritability, restlessness, anorexia, sweating, sleep abnormalities, and the like.

The term "treating cognitive disorders" as used herein means providing relief from the symptoms of cognitive disorders including but not limited to memory loss, disintegration of personality and intellect, depression, paranoia, anxiety and other psychologic symptoms.

The preparation of the mixture of enantiomers, (e.g., racemic mixture) of ondansetron is disclosed in U.S. Pat. No. 4,695,578. The R(+) isomer of ondansetron, may be obtained by resolution of the mixture of enantiomers of ondansetron using conventional means such as an optically active resolving acid; see, for example, "Stereochemistry of Carbon Compounds" by E. L. Eliel (McGraw Hill 1962) and Lochmuller C. H. et al., *J. Chromatogr.*, 1975, Vol. 113, No. 3, Pg. 283–302.

The magnitude of a prophylactic or therapeutic dose of R(+) ondansetron in the acute or chronic management of disease will vary with the severity of the condition to be treated, and the route of administration. The dose, and perhaps dose frequency, will also vary according to the age, body weight, and response of the individual patient. In general, the total, daily dose ranges, for the conditions described herein, from about 0.01 mg to about 35 mg administered in divided doses orally, or by a slow intravenous injection or infusion. In cases of moderate to highly emetogenic chemotherapy, it may be expected that, an initial loading dose of between about 2 mg to about 10 mg given by slow intravenous injection or infusion over 15–30 minutes, immediately before the emetogenic chemotherapy, and followed by about 2 mg to about 8 mg given orally every eight hours for periods up to four to five days will elicit therapy and provide for a reduction of symptoms. In cases of radiotherapy, and as an oral therapeutic for the other conditions described herein, generally doses of between about 2 mg to about 8 mg orally every eight hours, should provide benefit to adult patients. In the case of using R(+) ondansetron to treat cognitive disorders such as dementia and age-associated memory impairment, the total daily dosage ranges may be from about 0.001 mg to about 35 mg in divided doses orally or by a slow intravenous injection or infusion. Children generally will benefit from doses that are generally some 25–50 percent those of the adult for a given condition, while geriatric patients generally tolerate adult doses. It may be necessary to use dosages outside these ranges in some conditions.

The term, "an amount sufficient to alleviate the nausea and vomiting but insufficient to cause said adverse effects" is encompassed by the above described dosage amounts and dose frequency schedule. In addition, the term "an amount sufficient to alleviate said condition but insufficient to cause said adverse effects" wherein said conditions include but are not limited to behavioral disorders such as mood anxiety and schizophrenia as well as disturbances of neuronal 5-HT function including, but not limited to, disorders of gastrointestinal motility, depression, migraine and alcohol, nicotine or drug (benzodiazepine et al.) withdrawal are also encompassed by the above described amounts. The term "an amount sufficient to alleviate said condition but insufficient to cause said adverse effects" wherein said condition includes cognitive disorders such as dementia and age-associated memory impairment, is also encompassed by the above-described amounts.

Any suitable route of administration may be employed for providing the patient with an effective dosage of R(+) ondansetron. For example, oral, rectal, parenteral, transdermal, subcutaneous, intramuscular, and the like may be employed. Dosage forms include tablets, troches, dispersions, suspensions, solutions, capsules, patches, and the like.

The pharmaceutical compositions of the present invention comprise R(+) ondansetron as active ingredient, or a pharmaceutically acceptable salt thereof, and may also contain a pharmaceutically acceptable carrier, and optionally, other therapeutic ingredients. The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids including inorganic and organic acids. Such acids include acetic, benzene-sulfonic, benzoic camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are hydrobromic, hydrochloric, phosphoric and sulfuric acids.

The compositions include compositions suitable for oral, rectal or other mucosal routes, transdermal, parenteral (including subcutaneous, intramuscular, and intravenous), although the most suitable route in any given case will depend on the nature and severity of the condition being treated. The most preferred routes of the present invention include both intravenous injections, and infusions and the oral route. They may be conveniently presented in unit dosage form, and prepared by any of the methods well known in the art of pharmacy.

In the case where an oral composition is employed, a suitable dosage range for use is, e.g., from about 5 mg to about 35 mg total daily dose, administered as equally divided doses, three times a day. Preferably, a dose range of between about 10 mg to about 30 mg per day, administered as equally divided doses, three times a day, and most preferably from between about 12 mg to about 24 mg per day, administered as equally divided doses, three times a day. Patients may be upwardly titrated within this dose range to enable the satisfactory control of symptoms. In the case where an oral composition is employed to treat cognitive disorders such as dementia and age-associated memory impairment, a suitable dosage range for use is from about 0.001 mg to about 35 mg total daily dose administered as equally divided doses from one to three times a day. Preferably a dose range of between about 0.001 mg to about 20 mg per day administered as equally divided doses one to three times a day and most preferably from between 0.001 mg to about 10 mg per day administered as equally divided doses, one to three times a day.

In the case where an intravenous injection or infusion composition is employed, a suitable dosage range for use is, e.g. from about 0.01 mg to about 32 mg total daily dose, presented as a loading slow intravenous injection of about 2 mg to about 8 mg over 15–30 minutes, followed by an intravenous infusion of about 0.5 mg to about 1.0 mg/hour for up to 24 hours. These regimens may be followed by oral doses of between about 1.5 mg to about 8.0 mg every eight hours for periods up to five days.

In practical use, R(+) ondansetron can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous injections or infusions). In preparing the compositions for oral dosage form, any of the usual pharmaceutical media may be employed, e.g., water, glycols, oils, alcohols, flavoring agents, preservatives, coloring agents, and the like in the case of oral liquid preparations, e.g., suspensions, solutions, and elixirs; or aerosols; or carriers such as starches, sugars, micro-crystalline cellulose, diluents, granulating agents, lubricants, binders, disintegrating agents, and the like in the case of oral solid preparations e.g., powders, capsules, and tablets, with the solid oral preparations being preferred over the liquid preparations. The most preferred solid oral preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Another preferred route of administration, particularly to avoid problems associated with emesis, is transdermal delivery, for example, via an abdominal skin patch.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association, the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound, moistened with an inert liquid diluent. Desirably, each tablet contains from about 2.0 mg to about 8.0 mg of the active ingredient, and each cachet or capsule contains from about 2.0 mg to about 8.0 mg. of the active ingredient. Most preferably, the tablet, cachet or capsule contains either one of three dosages: 2.0 mg, 4.0 mg and 8.0 mg (as scored tablets, the preferable dose form) of active ingredient. Furthermore, each tablet or capsule can contain from about 0.001 mg to about 10.0 mg of the active ingredient. However, the amount of active ingredient found in the composition may vary depending on the amount of active ingredient to be administered to the patient.

The invention is further defined by reference to the following examples describing in detail, the preparation of the compound, and the compositions of the present invention. It will be apparent to those skilled in the art, that many modifications, both to materials and methods, may be practiced without departing from the purpose and interest of this invention.

All temperatures are in degrees Celsius.

EXAMPLES

EXAMPLE 1

A pharmacological study to determine the relative potency and specificity of optically pure R(+) ondansetron and racemic ondansetron as competitive antagonists at serotonin receptor subtype 5-$HT_3$ present in gastrointestinal, brain, and other tissues.

The optically pure and racemic compounds may be evaluated as a function of their molar concentration, for their relative abilities to inhibit the binding of $^3H$-5-HT in such selected preparations as nerves of guinea pig ileum and preparations of brain tissue from several species including rats and humans. The availability of 3H-5-HT as a radioligand with relatively high specific activity, the development of other selective 5-$HT_3$ antagonists, and the additional agonist, 2-methyl-5-hydroxy-tryptamine (2-methyl-5-HT) provide the pharmacologic tools for the characterization of the 5-$HT_3$ receptor, and the evaluation of R(+), and racemic ondansetron. (see Frazer, A., et al., Annu. Rev. Pharmacol. Toxicol. 30, 307–348, 1990). It has been suggested, (Bradley, P.B et al., Neuropharmacology 25, 563–576, 1986) as part of the evolving characterization of serotonin receptor subtypes, that responses mediated by 5-$HT_3$ receptors: be reduced by selective antagonists, not be inhibited by selective antagonists of other subtypes of serotonin receptors, and be mimicked by 2-methyl 5-HT at concentrations comparable to that of serotonin.

Accordingly, the comparative ability of R(+) and racemic ondansetron, to inhibit the binding of $^3H$-5-HT and the agonist, $^3H$-2-methyl 5-HT, not to be inhibited as a radioligand for 5-$HT_3$ receptors by selective antagonists of other subtypes and to be inhibited from selective binding as a function of concentration, by other 5-$HT_3$ selective antagonists of possibly greater potency including zacopride, ICS 205-930, and granisetron, will serve a characterization of potency and specificity at 5-$HT_3$ receptors.

EXAMPLE 2

ORAL FORMULATION

Tablet:

|  | Quantity per Tablet in mg | | |
|---|---|---|---|
| Formula | A | B | C |
| Active Ingredient R(+) ondansetron | 2.0 | 4.0 | 8.0 |
| Lactose BP | 151.5 | 149.5 | 145.5 |
| Starch BP | 30.0 | 30.0 | 30.0 |
| Pregelatinized Maize Starch BP | 15.0 | 15.0 | 15.0 |
| Magnesium Stearate BP | 1.5 | 1.5 | 1.5 |
| Compression Weight | 200.0 | 200.0 | 200.0 |

The active ingredient, is sieved through a suitable sieve and blended with lactose, starch, and pregeatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

EXAMPLE 3

ORAL FORMULATION

|  | mg/capsule | | |
|---|---|---|---|
| Formula | A | B | C |
| Active Ingredient R(+) ondansetron | 2.0 | 4.0 | 8.0 |
| Starch 1500 | 97.0 | 95.0 | 91.0 |
| Magnesium Stearate BP | 1.0 | 1.0 | 1.0 |
| Compression Weight | 100.0 | 100.0 | 100.0 |

The active ingredient is sieved and blended with the excipients. The mix is filled into size No. 2 hard gelatin capsules using suitable machinery. Other doses may be prepared by altering the fill weight an if necessary changing the capsule size to suit.

EXAMPLE 4

INTRAVENOUS FORMULATION

| Formula | µg/ml |
|---|---|
| Active Ingredient R(+) ondansetron | 400 |
| Dilute Hydrochloric Acid BP | to pH 3.5 |
| Sodium Chloride Injection BP | 1 ml |

What is claimed is:

1. A method of eliciting an antiemetic effect while avoiding the concomitant liability of adverse effects, which comprises administering to a human in need of antiemetic therapy, an amount sufficient to alleviate nausea and vomiting, but insufficient to cause said adverse effects, of R(+) ondansetron, or a pharmaceutically acceptable salt thereof, substantially free of its S(−) stereoisomer.

2. The method of claim 1, wherein R(+) ondansetron is administered by intravenous infusion, transdermal delivery, orally as a tablet or a capsule.

3. The method according to claim 2, wherein the amount administered is about 0.01 mg to about 35.0 mg.

4. The method according to claim 3, wherein the amount administered by intravenous infusion is about 2 mg to about 10 mg.

5. The method according to claim 3, wherein the amount administered orally is about 10.0 mg to about 30.0 mg.

6. The method according to claim 5, wherein the amount administered orally is about 12.0 mg to about 24.0 mg.

7. The method according to claim 1, wherein the amount of R(+) ondansetron, or a pharmaceutically acceptable salt thereof, is greater than approximately 90% by weight and 10% by weight or less of S(−) ondansetron.

8. The method according to claim 1, wherein R(+) ondansetron or a pharmaceutically acceptable salt thereof, substantially free of its S(−) stereoisomer, is administered together with a pharmaceutically acceptable carrier.

9. A method according to claims 2, 3, 4, 5, or 6, wherein R(+) ondansetron hydrochloride is administered.

* * * * *